United States Patent
Murdock et al.

(10) Patent No.: US 11,241,405 B2
(45) Date of Patent: Feb. 8, 2022

(54) METHODS TO ENHANCE A NON-SURGICAL MEDICAL TREATMENT

(71) Applicant: Anti-Plasmin Technologies, LLC, Dallas, TX (US)

(72) Inventors: Frank Murdock, Dallas, TX (US); Rodney James Rohrich, Dallas, TX (US); W. Paul Stewart, Dallas, TX (US)

(73) Assignee: Anti-Plasmin Technologies, LLC, Dallas, TX (US)

(*) Notice: Subject to any disclaimer, the term of this patent is extended or adjusted under 35 U.S.C. 154(b) by 54 days.

(21) Appl. No.: 16/576,585

(22) Filed: Sep. 19, 2019

(65) Prior Publication Data
US 2020/0046663 A1    Feb. 13, 2020

Related U.S. Application Data

(63) Continuation-in-part of application No. PCT/US2018/026086, filed on Apr. 4, 2018.

(60) Provisional application No. 62/481,162, filed on Apr. 4, 2017.

(51) Int. Cl.
| A61K 31/195 | (2006.01) |
| A61K 9/00   | (2006.01) |
| A61K 9/06   | (2006.01) |
| A61K 47/36  | (2006.01) |
| A61L 15/44  | (2006.01) |

(52) U.S. Cl.
CPC .......... *A61K 31/195* (2013.01); *A61K 9/0014* (2013.01); *A61K 9/06* (2013.01); *A61K 47/36* (2013.01); *A61L 15/44* (2013.01)

(58) Field of Classification Search
CPC ...... A61K 31/195; A61K 9/0014; A61K 9/06; A61K 47/36; A61K 31/454; A61K 38/57; A61K 2800/91; A61K 8/64; A61K 8/735; A61K 31/197; A61K 8/44; A61L 15/44; A61P 7/04; A61Q 19/08
See application file for complete search history.

(56) References Cited

U.S. PATENT DOCUMENTS

| 2002/0049471 | A1  | 4/2002  | Boethius |
| 2008/0260878 | A1* | 10/2008 | Harano .............. A61K 31/7036 424/764 |
| 2011/0171311 | A1  | 7/2011  | Gousse et al. |
| 2014/0105959 | A1* | 4/2014  | Paliwal ............... A61K 9/7038 424/449 |
| 2016/0074510 | A1  | 3/2016  | Murdock |

FOREIGN PATENT DOCUMENTS

WO    WO-00/37071 A1    6/2000

OTHER PUBLICATIONS

Byun, Sang-Young et al.; "Significant improvement in crow's feet after treatment with Jet-M and a mixed solution of copper-GHK, oligo-hyaluronic acid, rhodiolar extract, tranexamic acid, and β-glucan (GHR formulation)"; Journal of Cosmetic and Laser Therapy; vol. 18 Iss 5; Sep. 30, 2016; pp. 293-295 *abstract*.

* cited by examiner

*Primary Examiner* — Quanglong N Truong
(74) *Attorney, Agent, or Firm* — Winstead PC

(57) ABSTRACT

In an embodiment, the present disclosure relates to a method to enhance a non-surgical medical treatment, the method including applying a composition having an antifibrinolytic agent to an area of skin for non-surgical medical treatment, where the applying is at least one of before, during, and after the non-surgical medical treatment, beginning the non-surgical medical treatment to the area of skin, and continuing the non-surgical medical treatment until the non-surgical medical treatment is completed. In some embodiments, the antifibrinolytic agent is tranexamic acid at a concentration of about 20% (w/v). In some embodiments, the method further includes minimizing, by the antifibrinolytic agent, bruising caused by the non-surgical medical treatment. In an additional embodiment, the present disclosure relates to a composition to enhance a non-surgical medical treatment, the composition having an antifibrinolytic agent. In a further embodiment, the present disclosure relates to a kit having a carrier and an antifibrinolytic agent.

23 Claims, No Drawings

METHODS TO ENHANCE A NON-SURGICAL MEDICAL TREATMENT

CROSS-REFERENCE TO RELATED APPLICATIONS

This patent application is a continuation-in-part of PCT/US2018/026086, filed on Apr. 4, 2018. PCT/US2018/026086 claims priority from, and incorporates by reference the entire disclosure of, U.S. Provisional Application No. 62/481,162 filed on Apr. 4, 2017.

TECHNICAL FIELD

The present disclosure relates generally to a non-surgical medical treatment and more particularly, but not by way of limitation, methods and compositions to enhance a non-surgical medical treatment.

BACKGROUND

In the course of non-surgical medical treatments, such as those associated with cosmetic or dermatology procedures, patients can be subject to unwanted swelling, inflammation and/or bruising that is associated with a treatment, for example, the injection of fillers or neurotoxins, or the application of chemical peels, acne treatments, dermabrasion techniques and laser skin treatments. With respect to injection-type treatments, the needle and pressure can cause slight bleeding, and to counter this activity, certain vasoconstriction agents, such as epinephrine, can be applied to the tissue to reduce the size of blood vessels prior to injection, thereby making it less likely to be injured during a treatment, as well as reduce the amount of bleeding due to the size of the constricted blood vessel. However, vasoconstriction agents, such as epinephrine, can have a "rebound effect" which can create unwanted effects as the drug wears off and the vessels return to their normal state.

SUMMARY OF THE INVENTION

In an embodiment, a method to enhance a non-surgical medical treatment, the method including applying a composition having an antifibrinolytic agent to an area of skin for non-surgical medical treatment, where the applying is at least one of before, during, and after the non-surgical medical treatment, beginning the non-surgical medical treatment to the area of skin, and continuing the non-surgical medical treatment until the non-surgical medical treatment is completed.

In another embodiment, a method to enhance a non-surgical medical treatment, the method including applying a composition having an antifibrinolytic agent to an area of skin for non-surgical medical treatment, where the applying is at least one of before, during, and after the non-surgical medical treatment, and where the antifibrinolytic agent includes tranexamic acid in an amount of about 20% (w/v), beginning the non-surgical medical treatment to the area of skin, continuing the non-surgical medical treatment until the non-surgical medical treatment is completed, and minimizing, by the antifibrinolytic agent, bruising caused by the non-surgical medical treatment.

In an additional embodiment, the present disclosure relates to a composition to enhance a non-surgical medical treatment, the composition including an antifibrinolytic agent.

In a further embodiment, the present disclosure relates to a kit having a carrier and an antifibrinolytic agent.

DETAILED DESCRIPTION

In various embodiments, methods and compositions are used to enhance non-surgical medical treatments that are susceptible to bruising, swelling, inflammation or similar occurrences, the method includes applying an antifibrinolytic agent to an area of the skin within which the non-surgical medical treatment is performed, with the agent being applied prior to, during and/or following the non-surgical medical treatment. In certain embodiments, there are a number of additional non-surgical cosmetic and dermatological treatments that involve bruising, swelling and inflammation, such as chemical peels, dermabrasion, acne treatments and laser skin treatments.

In a professional survey of 100 plastic surgeons, dermatologists, and other practitioners performing a high volume of dermal filler procedures, over thirty-eight per week, 65% of the survey participants responded that they would routinely use a product in dermal filler procedures that reduces bruising by 50 to 60%. In addition, many of the participants responded that they would use such a product in a variety of other non-surgical procedures, such as, but not limited to, laser skin resurfacing (81%), chemical peels (49%), pulsed light treatment (41%), microdermabrasion (38%), laser hair removal (30%), acne treatments, tattoo removal, and the like. As such, there is a need for methods and compositions to reduce and/or eliminate bruising in patients undergoing non-surgical medical treatments.

Various embodiments of the present invention will now be described more fully with reference to the accompanying tables. The invention may, however, be embodied in many different forms and should not be construed as limited to the embodiments set forth herein.

An object of the present invention is to provide methods and compositions to minimize or reduce swelling, inflammation, bruising, or combinations of same and the like, resulting from a non-surgical treatment which can thereby enhance the non-surgical treatment. A further object of the present invention is to enhance a non-surgical medical treatment using dermal fillers and toxins by extending the duration/function of the non-surgical medical treatment. In certain embodiments, the present invention can be utilized with a number of non-surgical cosmetic and dermatological treatments that involve bruising, swelling and inflammation, such as chemical peels, dermabrasion, acne treatments and laser skin treatments. As used herein, a non-surgical medical treatment can involve various treatments, including, but not limited to, cosmetic or dermatologic procedures to improve physical appearance for aesthetic reasons, treatments to repair the effects of injury, disease or malfunctions, including medicines, physical and radiation therapies, and are typically non-invasive in nature, for example, a medical treatment with no linear incisions of the skin. In some embodiments, the cosmetic or dermatologic procedures can include, without limitation, dermal filler procedures, neuromodulator injections, laser skin resurfacing, chemical peels, pulsed light treatments, microdermabrasion, laser hair removal, acne treatments, tattoo removal procedures, or combinations of the same and like.

In accordance with the present invention, the non-surgical medical treatment is enhanced by the administration of an antifibrinolytic agent, or agents, before, during and/or after the non-surgical medical treatment of a human patient. As used herein, the term "enhance" means minimizing or reducing swelling, inflammation, bruising or combinations of same and the like, and may also involve extending the duration/function of dermal fillers and toxins. A practice of the present invention could be to utilize an antifibrinolytic agent, or agents, prior to a non-surgical treatment to provide for less swelling, inflammation and/or bruising, while further providing rapid and effective healing, for example, by limiting fibrinolytic activity, such as the conversion of plasminogen to plasmin, in or around the treatment area to thereby enhance the non-surgical medical treatment.

An antifibrinolytic agent can be provided to mitigate swelling, inflammation, bruising, or combinations of same and the like, that may be associated with a non-surgical medical treatment, such as, injections and/or applications of therapeutic, cosmetic, or dermatologic treatments. The antifibrinolytic agent may be a simple aqueous solution, or it may be combined with a pharmaceutically acceptable carrier, for example, gels, lotions, ointments, or creams, and may optionally contain other active or inactive treatment ingredients and/or preservatives. In some embodiments, the gels can be a gel or gel-like material. In some embodiments, the gel can include, without limitation, xanthan gum, hydroxyethylcellulose, or combinations thereof. In some embodiments, a hydroxyethylcellulose formulation can improve shelf-life stability and user-friendliness. In some embodiments, the antifibrinolytic agent can be combined with, for example, excipients to alter pH, excipients to provide stability, various preservatives, excipients for coloring, or other excipients for varying uses known to those of ordinary skill in the art. The solution and/or compound can be administered directly on, or into, the skin days, hours or minutes prior to the injection or application of a non-surgical medical treatment, during the treatment and/or following the treatment to minimize swelling, inflammation and/or bruising subsequent to the treatment. In some embodiments, the antifibrinolytic agent solution and/or compound can be pre-soaked on, for example, towelettes or gauze, for use when applying the antifibrinolytic agent before, during, and/or after a non-surgical medical treatment. In some embodiments, a towelette pre-soaked with tranexamic acid is utilized for application of the composition to the skin. In some embodiments, pre-soaked gauze is utilized for application of the composition to the skin. The antifibrinolytic agent may also be delivered systemically to provide similar cosmetic and/or healing benefits in non-surgical medical procedures. In certain embodiments, a combination of topical and systemic administration may be used.

For intravenous administration of one common antifibrinolytic agent, tranexamic acid (TA), the minimum dosage for the agent is about 10 mg/kg body weight. A more common dosage is about 10 mg/kg body weight prior to treatment, and 1 mg/kg/hour for 12 hours thereafter if continuous infusion is used. If a continuous infusion is not used, a second bolus of 10 mg/kg either at the end of treatment or after about 8 hours following the initial dose, is administered. The maximum dose is about 80 mg/kg in total amount given during the course of the treatment. The dose should be administered about 10-30 minutes prior to the start of treatment. With respect to trauma events, dosings should be administered within 3 hours following the event.

For oral administration, about half of the TA ingested does not enter the blood, so the minimum and maximum doses would be twice the amount for IV administration. For indications like heavy menstrual bleeding, repeat administration should occur about every 8 hours for up to 5 days.

Dosages for another common antifibrinolytic agent, epsilon-aminocaproic acid, are approximately ten times the dosage for tranexamic acid.

For the purpose of the present invention, the antifibrinolytic agent can act prophylactically, due to its continued activity in the tissue, to prepare and protect the treatment area for subsequent non-surgical medical treatments, as well as to facilitate a rapid and improved healing process after non-surgical medical treatments. The agent could be applied and composed in such a manner that it would not negatively affect the treatment and/or injection materials. In various embodiments, the agent can be delivered subsequent to an injection, for example, to continue the therapy throughout the post-procedure period where delayed bruising, inflammation and/or swelling might occur, for example, over 2 to 7 days.

The present invention can be practiced where the antifibrinolytic agent is administered after the non-surgical medical treatment has started, without prior administration of the antifibrinolytic agent. In such practice, the agent would be administered during and/or after the non-surgical medical treatment. When administered after the non-surgical medical treatment, such administration should be promptly done, such as within one hour, for example, after the non-surgical medical treatment is completed. Further, the present invention could be practiced by combining the antifibrinolytic agent with the treatment materials being injected. For example, tranexamic acid and hyaluronic acid could be combined to form the injected materials, with or without a prior administration of an antifibrinolytic agent. In some embodiments, the antifibrinolytic agent can be combined with, for example, a cross-linked hyaluronic acid polymer, sodium hyaluronate, dermal fillers, neurotoxins, hyaluronic acid, or combinations thereof. In some embodiments, the antifibrinolytic agent can be aprotinin, tranexamic acid, epsilon-aminocaproic acid (EACA), Kunitz domain (KD1) inhibitor, AZD 6564, mimetics, and analogues or derivatives of the same. In some embodiments, the antifibrinolytic agent can be a mimetic, an analogue, or derivative of tranexamic acid.

Antifibrinolytic agents have been shown to improve the hemostasis process during surgery due to the ability of the agent to reduce clot lysis, or breakdown. Antifibrinolytic agents have also been shown to be effective at reducing bleeding and transfusions in patients with hemophilia who undergo dental extractions. In addition, antifibrinolytic agents have been shown to reduce heavy menstrual bleeding when administered orally.

The present invention utilizes the activity of the antifibrinolytic agent prior to, during and/or optionally post-treatment, in order to avoid or reduce unwanted bruising, inflammation and/or swelling in non-surgical procedures. The present invention recognizes that the activity of the agent to reduce inflammation, bruising, and/or swelling is not necessarily solely an antifibrinolytic function or solely related to a reduction in bleeding, but can further involve a protective and healing effect by improving the tissue environment in the non-surgical medical treatment area such that healing is accelerated and a return to a more normal pre-treatment condition is stimulated.

In various embodiments, a method of treating humans with an antifibrinolytic agent prior to a non-surgical medical treatment can be utilized in order to reduce post-treatment inflammation, bruising, and/or swelling. In certain embodiments, the method includes utilizing a pharmaceutical composition containing an antifibrinolytic agent. In some embodiments, the pharmaceutical composition is a solution having a concentration of up to 30% (w/v) of an antifibrinolytic agent, and can, optionally be in a pharmaceutically acceptable carrier in which the solution can be adaptable for use on human skin. In various embodiments, the concentration can be up to 60% (w/v) of the antifibrinolytic agent. In some embodiments, the antifibrinolytic agent is in a concentration of about 20% (w/v). In particular embodiments, the antifibrinolytic agent is tranexamic acid in a concentration of about 20% (w/v).

In certain embodiments, the pharmaceutical composition antifibrinolytic agent is tranexamic acid, which can also, optionally be in a pharmaceutically acceptable carrier that can adapt to human skin. In other embodiments, the antifibrinolytic agent can be administered prior to the injection of a non-surgical medical treatment in order to reduce post-injection inflammation, bruising and/or swelling. In other embodiments, the agent can be applied and composed in such a manner that it does not negatively impact subsequent treatments.

In various embodiments, a method of treating humans with an antifibrinolytic agent prior to, during and/or post non-surgical medical treatment can be utilized in order to reduce inflammation, bruising and/or swelling. In certain embodiments, a non-surgical medical treatment can be enhanced by the antifibrinolytic agent thereby providing the benefit of extending the duration/function of dermal fillers and toxins. In various embodiments, a solution containing an antifibrinolytic agent can be utilized in order to reduce inflammation, bruising and/or swelling and can have a limited application time, for example, 3 minutes. In other embodiments, the solution can have an application time ranging from approximately 2 to 5 minutes. In certain embodiments, the solution application time can range from 3 to 10 minutes.

Dermal fillers, for example, JUVEDERM® and RESTYLANE®, used in cosmetic/dermatologic treatments, typically contain hyaluronic acid. Dermal fillers are typically injected into the skin (e.g., mid to deep dermis in the cheeks, around the eyes or the lip/perioral area) and act to provide volume to the injected area, leaving a more youthful appearance. Dermal filler treatment effects usually last 6 to 12 months. Toxins used in cosmetic/dermatologic treatments typically contain neurotoxins, for example, BOTOX®. These toxins are typically injected into the skin (e.g., the glabella area) and act to relax the muscles of the face thereby reducing lines and wrinkles around the injected area, and the effects usually last 3 to 6 months.

It is contemplated that by inhibiting the conversion of plasminogen to plasmin, which breaks down a variety of substances, such as fibrin and collagen, antifibrinolytic agents could prolong the time it takes for the body to break down injected substances, for example, hyaluronic acid and/or various neurotoxins. By prolonging the time it takes for the body to break down injected substances, the present invention seeks to improve the performance of the injected agent. In certain embodiments, antifibrinolytic agents such as tranexamic acid can be utilized prior to a non-surgical medical treatment, for example, a dermal filler injection, to reduce swelling and bruising that typically result from the treatment. In other embodiments, antifibrinolytic agents such as tranexamic acid can be utilized post-treatment (e.g., after a dermal filler injection) to reduce bruising in the treated area.

To further investigate the role of antifibrinolytic agents in non-surgical medical treatments, high-performance liquid chromatography (HPLC) analysis was performed on tranexamic acid and a carrier containing hyaluronic acid (i.e. hyaluronan), which is a common substance used to create a gel-like consistency in products applied topically to the skin and could be a possible carrier for an antifibrinolytic agent in non-surgical medical treatments, as well as on a common hyaluronic acid dermal filler, which contain cross-linked hyaluronic acid polymers to give them greater longevity, to see whether there was a change in either form of hyaluronic acid when mixed with tranexamic acid. First a skin care product from ERACLEA® Skin Care containing 1% (w/v) hyaluronic acid polymer and preservatives was tested. After the HPLC profile of tranexamic acid and the ERACLEA® product were established, an amount of tranexamic acid was added to the ERACLEA® product giving a 3% (w/v) concentration of tranexamic acid. The analysis was carried out with fresh sample preparations being mixed and immediately injected into the HPLC system for analysis as well as sample preparations that were mixed and allowed to stand for a 20 minute time period prior to injection.

Interaction studies between tranexamic acid and hyaluronic acid polymer were further conducted via HPLC on samples of the same ERACLEA® product to which concentrations of 0.5% (w/v) tranexamic acid and 3% (w/v) tranexamic acid had been added several weeks before. HPLC analysis was further conducted by adding 3% (w/v) tranexamic acid to a hyaluronic acid dermal filler and, more particularly, JUVEDERM® filler. Similar to the above-mentioned study, the JUVEDERM® analysis was carried out with fresh sample preparations being immediately injected for analysis as well as sample preparations that were allowed to stand for a 20 minute time period prior to injection. None of the analyses showed any interaction between tranexamic acid and either form of hyaluronic acid polymer.

Further, HPLC analysis was carried out on hyaluronic acid filler, specifically JUVEDERM®, when mixed with human plasmin and with physiological saline. The objectives of these analyses were to demonstrate the degradation of hyaluronic acid filler, and in particular, the complete degradation of hyaluronic acid filler in a sample after treatment with human plasmin, with no effect when mixed with physiological saline. The foregoing analyses will now be described with respect to each analysis in further detail below.

HPLC Method Development for Tranexamic Acid

The sample preparation was prepared as follows: 100 µL of tranexamic acid (Source: AUROMEDICS®, concentration 100 mg/mL sterile solution) was taken out from vial via syringe and diluted to 1000 µL volume by adding an aqueous solution of 60:40 ratio, by volume, distilled water/acetonitrile. This stock solution was used multiple times to develop HPLC methods for comparison with hyaluronic acid polymer, filler and human plasmin. Table 1, shown below, represents ultraviolet (UV) results for tranexamic acid undergoing HPLC with a flow rate of 1 mL/min, a sample concentration of 10 mg/mL, and an injection volume of 10 µL, a wave length of 205 nm and a solvent system of 40:60 ratio, by volume, acetonitrile/distilled water. As can be seen below, the retention time is 2.280 min for tranexamic acid.

TABLE 1

| UV Results | | | | |
| --- | --- | --- | --- | --- |
| Retention Time | Area | Area % | Height | Height % |
| 2.280 | 31220907 | 100.00 | 4825881 | 100.00 |
| Totals | 31220907 | 100.00 | 4825881 | 100.00 |

HPLC Method Development for Hyaluronic Acid Polymer

The sample preparation was prepared as follows: 10 mg of hyaluronic acid polymer (Source: ERACLEA®, pure hydration) was weighed in 2.5 mL of auto sampler vial and diluted to 1000 μL volume by adding an aqueous solution of 60:40 ratio, by volume, distilled water/acetonitrile and used as a standard stock solution. Table 2, shown below, represents UV results for hyaluronic acid polymers undergoing HPLC with a flow rate of 1 mL/min, a sample concentration of 10 mg/mL, and an injection volume of 10 μL, a wave length of 205 nm and a solvent system of 40:60 ratio, by volume, acetonitrile/distilled water. As can be seen below, the retention time is 7.467 min for hyaluronic acid polymer.

TABLE 2

| | UV Results | | | |
|---|---|---|---|---|
| Retention Time | Area | Area % | Height | Height % |
| 7.467 | 6537978 | 100.00 | 795794 | 100.00 |
| Totals | 6537978 | 100.00 | 795794 | 100.00 |

Retention time differences calculated between tranexamic acid and hyaluronic acid polymer was 5.187 min utilizing the tranexamic acid retention time of 2.280 min and the hyaluronic acid polymer retention time of 7.467 min.

HPCL Study to Detect Any Binding Interaction of Tranexamic Acid with Hyaluronic Acid Polymer Table 3, shown below, represents the UV results for freshly prepared 3% (w/v) tranexamic acid in hyaluronic acid polymer immediately injected to undergo HPLC with a flow rate of 1 mL/min, a sample concentration of 10 mg/mL, and an injection volume of 10 μL, a wave length of 205 nm and a solvent system of 40:60 ratio, by volume, acetonitrile/distilled water. As can be seen below, the retention times are 2.217 min and 7.577 min for tranexamic acid and hyaluronic acid polymer, respectively.

TABLE 3

| | UV Results | | | |
|---|---|---|---|---|
| Retention Time | Area | Area % | Height | Height % |
| 2.217 | 1727195 | 19.92 | 190499 | 18.53 |
| 7.577 | 6942792 | 80.08 | 837835 | 81.47 |
| Totals | 8669987 | 100.00 | 1028334 | 100.00 |

Table 4, shown below, represents the UV results for freshly prepared 3% (w/v) tranexamic acid in hyaluronic acid polymer that was allowed to stand for 20 min before being injected to undergo HPLC with a flow rate of 1 mL/min, a sample concentration of 10 mg/mL, and an injection volume of 10 μL, a wave length of 205 nm and a solvent system of 40:60 ratio, by volume, acetonitrile/distilled water. As can be seen below, the retention times are 2.217 min and 7.577 min for tranexamic acid and hyaluronic acid polymer, respectively.

TABLE 4

| | UV Results | | | |
|---|---|---|---|---|
| Retention Time | Area | Area % | Height | Height % |
| 2.217 | 1727195 | 19.92 | 190499 | 18.53 |
| 7.577 | 6942792 | 80.08 | 837835 | 81.47 |
| Totals | 8669987 | 100.00 | 1028334 | 100.00 |

Based on the data collected from the tranexamic acid in hyaluronic acid polymer sample immediately injected to undergo HPLC and the sample that was allowed to stand for 20 minutes before being injected to undergo HPLC, there is no interaction between tranexamic acid with hyaluronic acid polymer over a 20 minute time period. To further illustrate that no interactions between tranexamic acid with hyaluronic acid polymer exist, further samples and varying concentrations underwent HPLC analysis.

Table 5, shown below, represents UV results for 3% (w/v) tranexamic acid in a solution containing 1% (w/v) hyaluronic acid polymer, supplied by Hylaco, LLC., several weeks prior to undergoing HPLC analysis. The HPLC was conducted with a flow rate of 1 mL/min, a sample concentration of 10 mg/mL, and an injection volume of 10 μL, a wave length of 205 nm and a solvent system of 40:60 ratio, by volume, acetonitrile/distilled water. As can be seen below, the retention times are 2.210 min and 7.520 min for tranexamic acid and hyaluronic acid polymer, respectively. Similarly, the data shown below suggests there is no interaction between tranexamic acid and this hyaluronic acid polymer when mixed in solution.

TABLE 5

| | UV Results | | | |
|---|---|---|---|---|
| Retention Time | Area | Area % | Height | Height % |
| 2.210 | 1551176 | 20.08 | 183071 | 19.62 |
| 7.520 | 6175358 | 79.92 | 750126 | 80.38 |
| Totals | 7726534 | 100.00 | 933197 | 100.00 |

Table 6, shown below, represents UV results for 0.5% (w/v) tranexamic acid in a solution containing 1% (w/v) hyaluronic acid polymer, supplied by Hylaco, LLC., several weeks prior to undergoing HPLC analysis. The HPLC was conducted with a flow rate of 1 mL/min, a sample concentration of 12.0 mg/mL, and an injection volume of 10 μL, a wave length of 205 nm and a solvent system of 60:40 ratio, by volume, acetonitrile/distilled water. As can be seen below, the retention times are 2.197 min and 7.593 min for tranexamic acid and hyaluronic acid polymer, respectively.

TABLE 6

| | UV Results | | | |
|---|---|---|---|---|
| Retention Time | Area | Area % | Height | Height % |
| 2.197 | 1222461 | 11.87 | 197696 | 15.40 |
| 7.593 | 9077617 | 88.13 | 1085696 | 84.60 |
| Totals | 10300078 | 100.00 | 1283392 | 100.00 |

Table 7, shown below, represents UV results for 0.5% (w/v) tranexamic acid in hyaluronic acid polymer (scratch sample), supplied by Hylaco, LLC., several weeks prior to undergoing HPLC analysis. The HPLC was conducted with a flow rate of 1 mL/min, a sample concentration of 11.6 mg/mL, and an injection volume of 10 μL, a wave length of 205 nm and a solvent system of 40:60 ratio, by volume, acetonitrile/distilled water. As can be seen below, the retention times are 2.170 min and 7.497 min for tranexamic acid and hyaluronic acid polymer, respectively.

TABLE 7

| UV Results | | | | |
| --- | --- | --- | --- | --- |
| Retention Time | Area | Area % | Height | Height % |
| 2.170 | 1829993 | 13.60 | 250210 | 15.06 |
| 7.497 | 11626123 | 86.40 | 1411177 | 84.94 |
| Totals | 13456116 | 100.00 | 1661387 | 100.00 |

The above-presented data indicates that tranexamic acid does not appear to interact with this form of hyaluronic acid polymer in an aqueous solution with a gel-like consistency for easy topical application. Thus tranexamic acid is shown to be compatible with carriers used in topical preparations. Further analysis was made to determine whether tranexamic acid would interact with hyaluronic acid in a cross-linked form used for dermal fillers, specifically one of a JUVEDERM® family filler, and could thus be suitable for use before and after non-surgical medical treatments to reduce inflammation, bruising and/or swelling when the non-surgical medical treatment utilizes hyaluronic acid dermal fillers.

HPLC Method Development for Hyaluronic Acid Filler

The sample preparation was prepared as follows: 13 mg of filler (Source: JUVEDERM® Vollere XC) was weighed in a 2.5 mL vial and diluted to 1000 μL volume by adding an aqueous solution of 60:40 ratio, by volume, distilled water/acetonitrile. Table 8, shown below, represents UV results for JUVEDERM® Vollere XC undergoing HPLC with a flow rate of 1 mL/min, a sample concentration of 13 mg/mL (from syringe), and an injection volume of 10 μL, a wave length of 205 nm and a solvent system of 40:60 ratio, by volume, acetonitrile/distilled water. As can be seen below, the retention times are 2.167 min, 3.420 min and 9.953 min for the filler, with the largest area represented by the 3.420 min retention time.

TABLE 8

| UV Results | | | | |
| --- | --- | --- | --- | --- |
| Retention Time | Area | Area % | Height | Height % |
| 2.167 | 993958 | 13.62 | 81482 | 10.56 |
| 3.420 | 6304189 | 86.38 | 690337 | 89.43 |
| 9.953 | 117 | 0.00 | 88 | 0.01 |
| Totals | 7298264 | 100.00 | 771907 | 100.00 |

Table 9, shown below, represents the UV results for freshly prepared 3% (w/v) tranexamic acid in JUVEDERM® filler immediately injected to undergo HPLC with a flow rate of 1 mL/min, a sample concentration of 10 mg/mL, and an injection volume of 10 μL, a wave length of 205 nm and a solvent system of 40:60 ratio, by volume, acetonitrile/distilled water. As can be seen below, the retention times are 2.327 min and 3.143 min for tranexamic acid and JUVEDERM® filler, respectively.

TABLE 9

| UV Results | | | | |
| --- | --- | --- | --- | --- |
| Retention Time | Area | Area % | Height | Height % |
| 2.327 | 1818080 | 25.45 | 208612 | 21.59 |
| 3.143 | 5326600 | 74.55 | 757587 | 78.41 |
| Totals | 7144680 | 100.00 | 966199 | 100.00 |

Table 10, shown below, represents the UV results for freshly prepared 3% (w/v) tranexamic acid in JUVEDERM® filler that was allowed to stand for 20 min before being injected to undergo HPLC with a flow rate of 1 mL/min, a sample concentration of 10 mg/mL, and an injection volume of 10 μL, a wave length of 205 nm and a solvent system of 40:60 ratio, by volume, acetonitrile/distilled water. As can be seen below, the retention times are 2.327 min and 3.143 min for tranexamic acid and JUVEDERM® filler, respectively.

TABLE 10

| UV Results | | | | |
| --- | --- | --- | --- | --- |
| Retention Time | Area | Area % | Height | Height % |
| 2.327 | 1818080 | 25.45 | 208612 | 21.59 |
| 3.143 | 5326600 | 74.55 | 757587 | 78.41 |
| Totals | 7144680 | 100.00 | 966199 | 100.00 |

Based on the data collected from the tranexamic acid in JUVEDERM® filler immediately injected to undergo HPLC and the sample that was allowed to stand for 20 minutes before being injected to undergo HPLC, there is no interaction between tranexamic acid with the filler over a 20 minute time period. Data suggests that if there is any interaction between tranexamic acid and dermal filler material, it would be demonstrated during their direct contact over 20 minutes, especially since there was no interaction between tranexamic acid and hyaluronic acid in the gel solution when in contact for several weeks.

To investigate the possible degradation of the hyaluronic acid filler caused by human plasmin, hyaluronic acid filler was analyzed using HPLC with the hyaluronic acid filler in contact with human plasmin, as well as bathed in physiological saline.

HPLC Study to Measure the Degradation of Hyaluronic Acid Filler in Contact with Human Plasmin The sample preparation was prepared as follows: 13 mg of filler (Source: JUVEDERM® Vollere XC) was weighed in a 2.5 mL vial and diluted to 1000 μL volume by adding an aqueous solution of 60:40 ratio, by volume, distilled water/acetonitrile. From this stock solution 100 μL was taken out and mixed with 100 μL of 5 U (0.5 mL) human plasmin (Source: Sigma Aldrich, Lot #17148421) and slowly shaken for 15 min, filtered and injected into the HPLC system. Table 11, shown below, represents UV results for the sample undergoing HPLC with a flow rate of 1 mL/min, a sample concentration of 13 mg/mL, and an injection volume of 10 μL, a wave length of 205 nm and a solvent system of 40:60 ratio, by volume, acetonitrile/distilled water. The data below suggests that there is a complete degradation of filler hyaluronic acid polymer after the treatment of human plasmin, as there is no retention peak at 3.14 min (i.e., the filler peak).

TABLE 11

| | UV Results | | | |
|---|---|---|---|---|
| Retention Time | Area | Area % | Height | Height % |
| 3.003 | 20274447 | 55.69 | 662692 | 25.27 |
| 3.900 | 16133924 | 44.31 | 1960052 | 74.73 |
| Totals | 36408371 | 100.00 | 2622744 | 100.00 |

Retention times of 3.003 min and 3.900 min are shown above, with the notable absence of a retention peak at 3.14 min. Table 11 demonstrates the complete degradation of filler hyaluronic acid polymer after treatment of human plasmin due to the absence of a retention peak at 3.14 min, which would appear if the filler had been present.

A comparison of the filler data with the human plasmin-treated filler data indicates that the retention peak at 3.14 is absent in the human plasmin-treated filler, while the retention peak is clearly observable in the filler. The data demonstrates the complete degradation of filler hyaluronic acid polymer after treatment of human plasmin.

HPLC Study to Measure the Degradation of Hyaluronic Acid Filler after Bathed in Physiological Saline The sample preparation was prepared as follows: 10 mg of filler (Source: JUVEDERM® Vollere XC) was weighed in a 2.5 mL vial and diluted to 1000 μL volume by adding an aqueous solution of 60:40 ratio, by volume, distilled water/acetonitrile. From this stock solution 100 μL was taken out and mixed with 100 μL of physiological saline (Source: Hospira, Inc., Lot 64-154-DK) and slowly shaken for 15 min, filtered and injected into the HPLC system. Table 12, shown below, represents UV results for the sample undergoing HPLC with a flow rate of 1 mL/min, a sample concentration of 10 mg/mL, and an injection volume of 10 μL, a wave length of 205 nm and a solvent system of 40:60 ratio, by volume, acetonitrile/distilled water. As can be seen below, the retention times are 2.353 min and 3.120 min.

TABLE 12

| | UV Results | | | |
|---|---|---|---|---|
| Retention Time | Area | Area % | Height | Height % |
| 2.353 | 5281424 | 54.39 | 714706 | 56.82 |
| 3.120 | 4428834 | 45.61 | 543064 | 43.18 |
| Totals | 9710258 | 100.00 | 1257770 | 100.00 |

Overview of Results

As shown above in the preceding discussion, tranexamic acid does not appear to interact with hyaluronic acid, whether in a gel form or in cross-linked form for use as a dermal filler, and could thus be suitable for use before and after non-surgical medical treatments to reduce inflammation, bruising and/or swelling when the non-surgical medical treatment involves a hyaluronic acid-based dermal filler.

As shown above, the mixture of tranexamic acid and JUVEDERM® was allowed to stand for 20 minutes, which is indication that there is no interaction between tranexamic acid and dermal filler material. In addition, there was no interaction between tranexamic acid and the hyaluronic acid in the ERACLEA® product when left in contact for several weeks, and cross-linked hyaluronic acid in dermal fillers is generally much more robust than hyaluronic acid that has not been cross-linked. In a dermal filler procedure, tranexamic acid will generally be in contact with the hyaluronic acid material in the skin no more than about 18 hours before the tranexamic acid is metabolized by the body.

Moreover, the data indicates usage of tranexamic acid may in fact increase the duration and efficacy of filler treatments, in vivo, as filler hyaluronic acid polymer is totally degraded by human plasmin, and antifibrinolytic agents, such as tranexamic acid, inhibit the conversion of plasminogen to plasmin.

Additionally, as will be discussed below, clinical studies indicate that the addition of tranexamic acid to non-surgical treatments have proven to reduce bruising and swelling, as compared to clinical studies conducted in the absence of antifibrinolytic agents, such as tranexamic acid.

Clinical Studies

A randomized, controlled, clinical evaluation of JUVEDERM® Ultra XC in the nasolabial folds was conducted over a two week time period (conducted by Allergan) and common treatment site responses, by severity and duration, were presented. The most common injection site responses for JUVEDERM® Ultra XC were redness, swelling, tenderness, firmness, lumps/bumps, discoloration and bruising. According to the study, overall, 86% of subjects reported swelling and 59% of subjects reported bruising.

In non-surgical use conducted over approximately a 1 year period, 318 patients were subjected to a solution with a 3% (w/v) concentration of tranexamic acid before and after injection of hyaluronic acid dermal filler. Less than 1% of patients reported instances of bruising and swelling, an exponential and unexpected decline when compared to hyaluronic filler treatments without the use of tranexamic acid. Three patients of the 318 reported instances of bruising or swelling.

As shown above in clinical use, tranexamic acid plays a vital role in the suppression of bruising and swelling. This can be attributed to the activity of antifibrinolytic agents at the injection-site of non-surgical medical treatments. Further, based on the above-presented laboratory data, antifibrinolytic agents can play a vital role in slowing down the breakdown of injected hyaluronic acid dermal filler, by inhibiting the conversion of plasminogen to plasmin.

Bruising Studies

Although use of a solution having a 3% (w/v) concentration of tranexamic acid used with non-surgical medical treatments (e.g. dermal filler procedures) showed positive results in that it indicated a very low percentage of patients experiencing bruising based on immediate observation, a study of additional concentrations of tranexamic acid used with non-surgical medical treatments was conducted. Specifically, patients undergoing dermal filler procedures were recorded for up to 48 hours after the dermal filler procedures to study varying concentration effects of tranexamic acid usage with the non-surgical medical procedures.

The study provided herein utilized concentrations of tranexamic acid ranging from about 3% (w/v) to about 20% (w/v). Specifically, tranexamic acid concentrations of 3% (w/v), 5% (w/v), 10% (w/v), and 20% (w/v) were applied before and after dermal filler procedures by swabbing the areas of skin to be treated with gauze soaked with a tranexamic acid solution, such as those disclosed herein, as well as a 3% (w/v) tranexamic acid solution applied before and after the dermal filler procedure, and by the patient at home for two days. Surprisingly, with the 48-hour observation time, a three-fold improvement in bruising incidence was observed for the 20% (w/v) tranexamic acid solution. Approximately 45% of patients experienced no bruising, compared to only about 15% for the other series of patients.

For the 20% (w/v) tranexamic acid solution, data was also gathered on the severity of bruising (none, mild, moderate, and severe) and then compared to the severity of bruising reported in the labeling for two of the most common dermal filler products, JUVEDERM VOLLURE™ XC and JUVEDERM VOLBELLA® XC, when administered without any antifibrinolytic agent. The comparison indicated that about 28% more patients experienced no bruising when a tranexamic acid solution was used. In addition, when bruising occurred, no patients bruised severely when the tranexamic acid solution was used, compared to almost 20% who bruised severely without a tranexamic acid solution, indicating a 100% improvement. Additionally, 67% of patients only bruised mildly with the tranexamic acid solution compared to 37% bruising mildly without a tranexamic acid solution, indicating an 80% improvement. Mild to no bruising combined constituted 82% of patients receiving the tranexamic acid solution, compared to 52% not receiving a tranexamic acid solution, indicating a 58% improvement.

In various embodiments, the antifibrinolytic agent can be aprotinin, tranexamic acid, epsilon-aminocaproic acid (EACA), a Kunitz domain (KD1) inhibitor, AZD 6564 and analogues or derivatives of the same. In various embodiments, the Kunitz domain inhibitor can be a Kunitz-type inhibitor similar to KD1.

In certain embodiments, EACA can be utilized as the antifibrinolytic agent in a solution up to 60% (w/v) EACA. In some embodiments, the concentration of EACA can range from about 7% (w/v) to about 60% (w/v).

In other embodiments, tranexamic acid can be utilized as the antifibrinolytic agent in a solution up to 30% (w/v) tranexamic acid. In various embodiments, the concentration of tranexamic acid can range from about 0.7% (w/v) to about 30% (w/v). In some embodiments, the tranexamic acid is about 3% (w/v). In some embodiments, the tranexamic acid is about 5% (w/v). In some embodiments, the tranexamic acid is about 10% (w/v). In some embodiments, the tranexamic acid is about 15% (w/v). In some embodiments, the tranexamic acid is about 20% (w/v). In some embodiments, the tranexamic acid is about 25% (w/v). In some embodiments, the tranexamic acid is about 30% (w/v).

In further embodiments, aprotinin can be utilized as the antifibrinolytic agent in a solution of at least 0.1% (w/v) aprotinin.

In still further embodiments, KD1 can be utilized as the antifibrinolytic agent in a solution of at least 0.1% (w/v) KD1.

In certain embodiments, AZD 6564 can be utilized as the antifibrinolytic agent in a solution of up to 15% (w/v). In further embodiments, the concentration of AZD 6564 can range from about 0.35% (w/v) to about 15% (w/v).

In some embodiments, the antifibrinolytic agent can include, without limitation, tranexamic acid, aprotinin, epsilon-aminocaproic acid (EACA), Kunitz domain (KD1) inhibitor, AZD 6564 analogs, derivatives, or mimetics.

In further embodiments, the present disclosure relates to a kit having a carrier and an antifibrinolytic agent packaged separately so as to be assembled on-site. In some embodiments, the kit includes a carrier and an antifibrinolytic agent. In some embodiments, the carrier and the antifibrinolytic agent are each individually packaged separately in sterile form. In some embodiments, the carrier can include, without limitation, a gel, a lotion, an ointment, a solution, or a cream. In some embodiments, a combination of the carrier and the antifibrinolytic agent produces at least one of a gel, a lotion, an ointment, a solution, and a cream having a concentration of up to 60% (w/v) of the antifibrinolytic agent in the combination. In some embodiments, the antifibrinolytic agent is tranexamic acid and the concentration of the combination is up to 30% (w/v) tranexamic acid. In some embodiments, the antifibrinolytic agent is tranexamic acid and the concentration of the combination is about 20% (w/v) tranexamic acid. In some embodiments, the kit further includes at least one of a towellette or gauze for application of a combination of the carrier and the antifibrinolytic agent. In some embodiments, the carrier includes, but is not limited to, at least one of an inactive ingredient, a preservative, a gel, a lotion, an ointment, a solution, a cream, hyaluronic acid, a cross-linked hyaluronic acid polymer, a dermal filler, a neurotoxin, and hydroxyethylcellulose.

Although various embodiments of the methods and compositions of the present disclosure have been illustrated in the accompanying tables and drawings, and described in the foregoing Specification, it will be understood that the invention is not limited to the embodiments disclosed, but is capable of numerous rearrangements, modifications, and substitutions without departing from the spirit and scope of the invention as set forth herein. It is intended that the Specification and examples be considered as illustrative only.

What is claimed is:

1. A method to enhance a non-surgical medical treatment, the method comprising:
    applying a composition comprising an antifibrinolytic agent to an area of skin subjected to the non-surgical medical treatment, wherein the applying occurs during at least one of before, during, or after the non-surgical medical treatment, and wherein the antifibrinolytic agent comprises tranexamic acid at a concentration of about 20% (w/v);
    beginning the non-surgical medical treatment to the area of skin;
    continuing the non-surgical medical treatment until the non-surgical medical treatment is completed; and
    minimizing, by the antifibrinolytic agent, bruising caused by the non-surgical medical treatment, wherein the applying occurs on the area of skin in which the non-surgical medical procedure is performed.

2. The method of claim 1, wherein the antifibrinolytic agent is part of a solution.

3. The method of claim 2, wherein the composition is applied as part of a pharmaceutically acceptable carrier which adapts the solution to human skin.

4. The method of claim 3, wherein the pharmaceutically acceptable carrier is at least one of a gel, a lotion, and a cream.

5. The method of claim 1, comprising combining the composition with a treatment material prior to beginning the non-surgical medical treatment to form a combined material, and wherein the beginning the non-surgical medical treatment comprises injecting the combined material to the area of skin being treated.

6. The method of claim 5, wherein the treatment material comprises at least one of hyaluronic acid, a cross-linked hyaluronic acid polymer, a dermal filler, and a neurotoxin.

7. The method of claim 1, comprising minimizing, by the antifibrinolytic agent, at least one of swelling and inflammation.

8. The method of claim 1, wherein the composition is delivered systemically.

9. The method of claim 1, comprising extending, by the antifibrinolytic agent, at least one of duration and function of the non-surgical medical treatment.

10. The method of claim 1, wherein the non-surgical medical treatment comprises an injection or application procedure selected from the group consisting of a cosmetic procedure, a dermatologic procedure, or combinations thereof.

11. The method of claim 1, wherein the non-surgical medical treatment is an injection of at least one of a dermal filler and a neurotoxin.

12. The method of claim 1, wherein the composition comprises at least one of an inactive ingredient, a preservative, a gel, hyaluronic acid, a cross-linked hyaluronic acid polymer, a dermal filler, a neurotoxin, and hydroxyethylcellulose.

13. The method of claim 1, wherein the applying utilizes at least one of gauze and a towelette pre-soaked with the composition.

14. A method to enhance a non-surgical medical treatment, the method comprising:
  applying a composition comprising an antifibrinolytic agent to an area of skin for non-surgical medical treatment, wherein the applying occurs during at least one of before, during, or after the non-surgical medical treatment, and wherein the antifibrinolytic agent comprises tranexamic acid at a concentration of about 20% (w/v);
  beginning the non-surgical medical treatment to the area of skin;
  continuing the non-surgical medical treatment until the non-surgical medical treatment is completed;
  minimizing, by the antifibrinolytic agent, bruising caused by the non-surgical medical treatment; and
  inhibiting, by the antifibrinolytic agent, conversion of plasminogen to plasmin to counteract breakdown of injected substances in the non-surgical medical treatment.

15. The method of claim 14, wherein the antifibrinolytic agent is part of a solution.

16. The method of claim 14, comprising combining the composition with a treatment material prior to beginning the non-surgical medical treatment to form a combined material, and wherein the beginning the non-surgical medical treatment comprises injecting the combined material to the area of skin being treated.

17. The method of claim 16, wherein the treatment material comprises at least one of hyaluronic acid, a cross-linked hyaluronic acid polymer, or a dermal filler.

18. The method of claim 14, comprising minimizing, by the antifibrinolytic agent, at least one of swelling and inflammation.

19. The method of claim 14, wherein the composition is delivered systemically.

20. The method of claim 14, comprising extending, by the antifibrinolytic agent, function of the non-surgical medical treatment.

21. The method of claim 14, wherein the non-surgical medical treatment comprises an injection or application procedure selected from the group consisting of a cosmetic procedure, a dermatologic procedure, and combinations thereof.

22. The method of claim 14, wherein the non-surgical medical treatment is an injection of a dermal filler.

23. The method of claim 14, wherein the composition comprises at least one of an inactive ingredient, a preservative, a gel, hyaluronic acid, a cross-linked hyaluronic acid polymer, a dermal filler, or hydroxyethylcellulose.

* * * * *